United States Patent
Perez Nunez

(10) Patent No.: US 11,638,647 B2
(45) Date of Patent: May 2, 2023

(54) PROSTHESIS FOR HIP REPLACEMENT WITH POLYETHYLENE HEAD AND ANTI-ROTATIONAL INTRA-PROSTHETIC ASSEMBLY

(71) Applicant: Rafael Eduardo Perez Nunez, Bogota (CO)

(72) Inventor: Rafael Eduardo Perez Nunez, Bogota (CO)

( * ) Notice: Subject to any disclaimer, the term of this patent is extended or adjusted under 35 U.S.C. 154(b) by 0 days.

(21) Appl. No.: 16/977,712

(22) PCT Filed: Mar. 9, 2018

(86) PCT No.: PCT/IB2018/051565
§ 371 (c)(1),
(2) Date: Sep. 2, 2020

(87) PCT Pub. No.: WO2019/171158
PCT Pub. Date: Sep. 12, 2019

(65) Prior Publication Data
US 2021/0007853 A1    Jan. 14, 2021

(51) Int. Cl.
*A61F 2/32* (2006.01)
*A61F 2/36* (2006.01)
(Continued)

(52) U.S. Cl.
CPC .............. *A61F 2/3609* (2013.01); *A61F 2/32* (2013.01); *A61F 2/34* (2013.01); *C08L 23/06* (2013.01);
(Continued)

(58) Field of Classification Search
CPC ........ A61F 2/3609; A61F 2/34; A61F 2/4014; A61F 2310/00017; A61F 2310/00023;
(Continued)

(56) References Cited

U.S. PATENT DOCUMENTS

| 4,380,090 A | * | 4/1983 | Ramos .................... A61F 2/32 623/22.2 |
| 5,133,764 A | | 7/1992 | Pappas et al. |

(Continued)

FOREIGN PATENT DOCUMENTS

| EP | 2324800 A1 | 5/2011 |
| ES | 2302824 T3 | 8/2008 |

OTHER PUBLICATIONS

International Search Report, dated Oct. 26, 2018 for corresponding International patent application No. PCT/IB2018/051565.
(Continued)

*Primary Examiner* — Dinah Baria
(74) *Attorney, Agent, or Firm* — Amster, Rothstein & Ebenstein LLP

(57) ABSTRACT

This invention corresponds to a prosthesis for total or hip resurfacing replacement, which comprises a prosthetic femoral head made of highly cross-linked polyethylene, with a diameter ranging from 38 mm to 64 mm, to articulate with a cup or acetabular component made of metal. When the invention applies to total hip replacement, the polyethylene head includes a metal core, which contains inside the female counterpart (14) to mate with the male counterpart (13) of a Morse taper, located at the upper end of the femoral component. The use of this type of head for total hip replacement, articulated with an ultra-polished acetabular cup, reduces the risk of dislocation, transmits less angular and torque forces to the Morse taper than large metal heads, and avoids the problems related to the metal-metal bearing or with the use of large metal heads with thin polyethylene. When the invention relates to hip resurfacing replacement, the highly cross-linked polyethylene femoral head has a lower polyethylene extension or stem with or without internal metal reinforcement (151) or a metal stem integrated into a metal-back (152). Using these types of heads for hip (Continued)

resurfacing replacement heads eliminates the problems associated with metal-on-metal resurfacing replacements.

13 Claims, 16 Drawing Sheets

(51) Int. Cl.
*A61F 2/34* (2006.01)
*C08L 23/06* (2006.01)
*A61F 2/30* (2006.01)

(52) U.S. Cl.
CPC .............. *A61F 2002/3093* (2013.01); *A61F 2002/30662* (2013.01); *A61F 2310/00017* (2013.01); *A61F 2310/00023* (2013.01); *A61F 2310/00029* (2013.01); *A61F 2310/00179* (2013.01); *C08L 2207/06* (2013.01); *C08L 2312/00* (2013.01)

(58) Field of Classification Search
CPC ............ A61F 2310/00029; A61F 2310/00179; A61F 2002/3093; A61F 2002/30662; A61F 2002/30367; A61F 2002/4037; A61F 2002/365; A61F 2002/3605; C08L 23/06; C08L 2207/06; C08L 2312/00
See application file for complete search history.

(56) References Cited

U.S. PATENT DOCUMENTS

| | | | | |
|---|---|---|---|---|
| 2011/0257759 | A1* | 10/2011 | Frazee | A61F 2/36 623/23.42 |
| 2012/0232667 | A1* | 9/2012 | Katrana | A61F 2/4014 623/19.12 |
| 2014/0094927 | A1 | 4/2014 | Weeden | |
| 2015/0250620 | A1* | 9/2015 | Brown | A61F 2/4684 623/22.15 |
| 2015/0289984 | A1 | 10/2015 | Budge | |
| 2017/0333192 | A1 | 11/2017 | Zhou et al. | |

OTHER PUBLICATIONS

International Preliminary Report on Patentability, dated May 7, 2020, or corresponding International patent application No. PCT/IB2018/051565.
Langton, D. J., Jameson, S. S., Joyce, T. J., Gandhi, J. N., Sidaginamale, R., Mereddy, P., . . . & Nargol, A. V. F. (2011). Accelerating failure rate of the ASR total hip replacement. The Journal of bone and joint surgery. British vol. 93(8), 1011-1016.
Meyer, H., Mueller, T., Goldau, G., Chamaon, K., Ruetschi, M., & Lohmann, C. H. (2012). Corrosion at the cone/taper interface leads to failure of large-diameter metal-on-metal total hip arthroplasties. Clinical Orthopaedics and Related Research®, 470(11), 3101-3108.
Cooper, H. J., Della Valle, C. J., Berger, R. A., Tetreault, M., Paprosky, W. G., Sporer, S. M., & Jacobs, J. J. (2012). Corrosion at the head-neck taper as a cause for adverse local tissue reactions after total hip arthroplasty. The Journal of bone and joint surgery. American vol. 94(18), 1655.
Loving, L., Herrera, L., Banerjee, S., Heffernan, C., Nevelos, J., Markel, D. C., & Mont, M. A. (2015). Dual mobility bearings withstand loading from steeper cup-inclinations without substantial wear. Journal of Orthopaedic Research, 33(3), 398-404.
Berry, D. J., Von Knoch, M., Schleck, C. D., & Harmsen, W. S. (2005). Effect of femoral head diameter and operative approach on risk of dislocation after primary total hip arthroplasty. JBJS, 87(11), 2456-2463.
Gaudin, G., Ferreira, A., Gaillard, R., Prudhon, J. L., Caton, J. H., & Lustig, S. (2017). Equivalent wear performance of dual mobility bearing compared with standard bearing in total hip arthroplasty: in vitro study. International orthopaedics, 41(3), 521-527.
Phillips, C. B., Barrett, J. A., Losina, E., Mahomed, N. N., Lingard, E. A., Guadagnoli, E., . . . & Katz, J. N. (2003). Incidence rates of dislocation, pulmonary embolism, and deep infection during the first six months after elective total hip replacement. JBJS, 85(1), 20-26.
Hamadouche, M., Arnould, H., & Bouxin, B. (2012). Is a cementless dual mobility socket in primary THA a reasonable option?. Clinical Orthopaedics and Related Research®, 470(11), 3048-3053.
Hart, A. J., Satchithananda, K., Liddle, A. D., Sabah, S. A., McRobbie, D., Henckel, J., . . . & Mitchell, A. W. (2012). Pseudotumors in association with well-functioning metal-on-metal hip prostheses: a case-control study using three-dimensional computed tomography and magnetic resonance imaging. JBJS, 94(4), 317-325.
Tower, S. S., Currier, J. H., Currier, B. H., Lyford, K. A., Van Citters, D. W., & Mayor, M. B. (2007). Rim cracking of the cross-linked longevity polyethylene acetabular liner after total hip arthroplasty. JBJS, 89(10), 2212-2217.
Philippot, R., Farizon, F., Camilleri, J. P., Boyer, B., Derhi, G., Bonnan, J., . . . & Lecuire, F. (2008). Survival of cementless dual mobility socket with a mean 17 years follow-up. Revue de Chirurgie Orthopédique et Réparatrice de l'Appareil Moteur, 94(8), e23-e27.
Langton, D. J., Sidaginamale, R., Lord, J. K., Nargol, A. V. F., & Joyce, T. J. (2012). Taper junction failure in large-diameter metal-on-metal bearings. Bone & joint research, 1(4), 56-63.

\* cited by examiner

A

B

A

B   C

PROSTHESIS FOR HIP REPLACEMENT WITH POLYETHYLENE HEAD AND ANTI-ROTATIONAL INTRA-PROSTHETIC ASSEMBLY

CROSS REFERENCE TO RELATED APPLICATIONS

This application is a national phase of PCT application No. PCT/IB2018/051565, filed Mar. 9, 2018, which is incorporated herein by reference thereto.

FIELD OF THE INVENTION

The present invention relates to a total hip or a hip resurfacing replacement prosthesis characterized in that it comprises a prosthetic femoral head, made of highly cross-linked polyethylene (HCLPE), with a diameter ranging from 38 mm to 64 mm, to articulate with a cup or acetabular component made of metal.

When the invention applies to total hip replacement, the polyethylene head is coupled to the cone of the femoral component, using an anti-rotational connector core that contains the female counterpart of the Morse taper, which is stably assembled in said head by means of a locking mechanism. The use of a large, highly cross-linked polyethylene head associated with an anti-rotational femoral connector core allows for a greater arc of movement, reducing the risk of dislocation while transmitting less angular and torque forces to the Morse taper than large metal heads. All this, without the biological problems related to the metal-metal combination or the use of thin polyethylene.

When the invention is applied to hip resurfacing replacement, the prosthetic femoral head made of highly cross-linked polyethylene is assembled into an anti-rotational metal-back that includes an extension or distal stem that allows fixation directly to the femoral neck with or without bone cement. The latter, while preserving the advantages of bone preservation, load transmission, stability and ease of revision of the resurfacing prostheses.

STATE OF THE ART

Total hip replacement is a surgery with a very high success rate in relieving pain and improving the functional capacity of patients with osteoarthritic processes in the hip joint. Current implant cementation techniques, the use of porous-coated implants for bone ingrowth, and the introduction of new low-wear materials prevent early loosening of the prosthesis and provide long-lasting fixation of the prosthesis. However, prosthetic instability continues to be a frequent cause of reoperation.

A total hip replacement prosthesis is composed of an acetabular component (2) and a femoral component (1), as shown in FIG. 1A. Both can be fixed to the patient's bone with bone cement (cemented prostheses) or without cement (uncemented prostheses). In the latter, fixation is achieved by the use of porous-coated implants that allow bone growth inside or roughness on its surface. This process is called osteo-integration.

Currently, the most commonly used acetabular components are uncemented and modular, where the porous coating for osteo-integration varies in its properties and composition depending on the manufacturer. These components are made up of an external metal shell or acetabular cup, which is fixed in the native acetabular cavity by press-fit, with the option of additional fixation with screws. An internal modular polyethylene or polyethylene liner (3) is attached to the acetabular cup (2), which presents on its articular side a hemispherical cavity to receive the metallic or ceramic femoral head (12) as shown in the FIG. 1A. These heads have a diameter of 22, 26, 28, 32, 36 or more millimeters.

The cemented femoral component of the total hip replacement is a smooth-surface or minimally rough metal stem that is fixed in the medullary canal of the femur by bone cement (polymethyl methacrylate), while the uncemented femoral component (1) is covered with a surface for osteo-integration, which varies in its extension, properties and composition, according to the manufacturer.

The femoral component (1) articulates with the acetabular polyethylene (3) through of a modular head (12), which can be metallic (12A) or ceramic (12B and 12C), as shown in FIG. 2. These heads (12) are assembled to the stem (11) by means of a Morse cone system consisting of a male component (13), located at the upper conical end of the femoral stem (11), and a female component (14), corresponding to a conical cavity of the femoral head (12), with minimum tolerance between the angle of the cone (13) of the stem and the angle of the conical cavity (14) in the head (12), to obtain a wide contact between the surfaces in order to achieve a firm and durable fixation, as illustrated in FIG. 3.

On the other hand, resurfacing hip replacement is the hip arthroplasty in which a metallic acetabular component with a large inner diameter (2) and ultra-polish inner surface is placed with a femoral component (1), which replaces only the articular surface of the femoral head (12). Currently, a metallic femoral component (1) is used with a stem (15) for fixation to the femoral neck (16), as shown in FIG. 1B. The advantages of this type of implant are that the bone resection is less, since the femoral neck does not have to be removed, the anatomy of the hip is better restored, the load transmission of to the proximal femur is optimized, there is less risk of dislocation and revision surgery becomes easier.

Both hip replacement and hip resurfacing replacement prostheses had undergone an evolutive process, aimed at improving their performance and avoiding wear of their components in order to offer the patient a more efficient and durable implant. In the search for improvement it has been established that a relevant variable is the material from which the surfaces of the prosthesis that support the load and the movement of the joint are made of.

Currently, the most widely used pairs of prosthetic movement surfaces are those shown in FIG. 2, which include metal heads against highly cross-linked polyethylene (2A), ceramic head against highly cross-linked polyethylene (2B) and ceramic head against a ceramic acetabular insert (2C). The latter is the one that shows less wear both in-vitro and in-vivo.

With the use of more wear-resistant materials, such as metal-metal, ceramic-ceramic, ceramic-HCLPE, metal-HCLPE pairs of friction, the use of larger diameter heads is introduced almost simultaneously in total hip replacement with the aim to improve the safe range of motion of the joint and decrease the incidence of prosthetic dislocation (disassembly of the prosthetic femoral head from its acetabular counterpart), which has been one of the main complications of total hip replacement. (Berry et al. Effect of the femoral head diameter and operative approach on risk of dislocation after primary total hip arthroplasty, Journal of Bone and Joint Surgery, 2005; 87-A (11): 2456), (Phillips et al. Incidence rates of dislocation, pulmonary embolism and deep infection during the first six months after elective total hip replacement. Journal of Bone and Joint Surgery, 2003; 85-A (1): 20).

In principle, it is considered that a larger prosthetic head increases the stability of the total hip replacement, because it increases the head-neck diameter ratio of the prosthesis and increases the impingement free range of motion, as evidenced in the FIGS. 4A and B. In addition, a larger diameter of the head increases the distance that the center of rotation of the prosthetic head has to displace in order to disengage from the cavity. Likewise, as this displacement is greater, the elongation of the soft tissues for dislocation to occur has to be greater, since they act as a restrictor for displacement and dislocation.

However, the use of large heads for total hip replacement has shown several drawbacks. The first of them is that with the use of a larger diameter head, without varying the diameter of the acetabular component, a thinner polyethylene or ceramic insert must be used, and thin components have shown an increased risk of failure due to accelerated wear or material fatigue.

Likewise, it has been found that the heads with a larger diameter, despite showing less linear wear, produce greater volumetric wear of the acetabular polyethylene and it is considered that a greater volume of particles generated in the joint can have negative consequences on the durability of the implant. This wear is less when low wear acetabular inserts (3) such as HCLPE or ceramics (FIG. 2) are used. However, these components are much more brittle than conventional polyethylene and have a higher risk of material failure, especially if their thickness is thin (Tower et al, Rim Cracking of the cross-linked Longevity acetabular liner after total hip arthroplasty. Journal of Bone and Joint Surgery, 2007; 89-A (10): 2212).

On the other hand, a head with a larger diameter could increase the torque and bending forces transmitted to the Morse taper, which joins the head with the femoral component, increasing the risk of local corrosive processes and the release of ions and metallic particles, with their local and systemic consequences. (Cooper et al. Corrosion at the Head-Neck Taper as a Cause for Adverse Local Tissue Reactions After Total Hip Arthroplasty. Journal of Bone and Joint Surgery, 2012; 94-A (18): 1655.

With metal on metal total hip replacement implants, in which the larger diameter metal femoral head articulates directly with an ultra-polished metal acetabular component (FIG. 5A), there were no fragility issues and the results in relation to short-term loosening and dislocation were good, but in the medium term, drawbacks appeared due to high levels of metal ions in the blood and catastrophic adverse local reactions, with large destruction of peri-prosthetic tissues, especially when big heads were used. (Meyer et al. Corrosion at the Cone/Taper Interface Leads to failure of Large-diameter metal-on-Metal Total Hip Arthroplasties. Clinical Orthopedics and Related Research, 2012; 470 (11): 3101); Langton et al. Taper Junction Failure in Large Diameter Metal on Metal Bearings. Bone Joint Research 2012, Vol. 1 (4): 56). In addition to the aforementioned failures, metal ion drawbacks and adverse reactions were also reported in metal-metal implants for hip resurfacing replacements, causing the use of both types of replacement devices to be abandoned or to be used only with very limited indications. (Langton et al. Accelerating failure rate of ASR total hip replacement. J. Bone Joint Surg (Br), 2011; 93B (8): 1011; Hart et al. Pseudotumors in Association with Well-Functioning Metal on Metal Hip Prostheses. J Bone Joint Surg (Am), 2012; 94: 317).

The cause of these problems seems to be a combination of punctual areas of load concentration on the articular surface of the implants with poorly positioned acetabular components (edge loading) and the generation of larger amounts of corrosion products at the Morse taper interface due to increased transmission of frictional torque and bending forces to the taper of the femoral component with large metal heads (FIG. 5B) compared to small heads (FIG. 5C), and even the development of instability in the interface between the head (12) and the femoral stem (11) (FIG. 3). For these reasons, large-head for metal-on-metal surfaces, such as those shown in FIG. 5A, have been abandoned.

In an attempt to improve mobility and stability, without using the metal-on-metal combination, dual mobility cups were introduced, a novel and attractive concept shown in FIGS. 6A, 6B and 6C. This alternative consists of assembling a smaller diameter metal or ceramic head in a larger diameter polyethylene mobile acetabular insert, which in turn articulates with an ultra-polished metal cup, that has an exterior surface for either cementing or porous coated. In this way, two mobility sites are generated, that is, two joints, as shown in FIG. 6. The main joint is given by the movement of the metal head (12) inside the polyethylene insert (3), and the secondary joint is represented by the movement between the mobile polyethylene (3) and the metal cup (2), thereby expanding the arc of movement.

It is important to clarify that the assembly of the metal head (12) in the polyethylene insert (3) is under pressure, using a capture mechanism to avoid dislocation. That is, the opening diameter of the polyethylene insert (3) is less than the diameter of the metal head (12), which requires some deformation of the polyethylene (3) during the assembly of the head, therefore in these type of implants the use of highly cross-linked polyethylene is not considered to be safe, even though they wear less, because they are more brittle to deforming forces.

With this type of implants the incidence of prosthetic dislocation in general has been reduced. However, there is a 0 to 5% of patients who present what has been called intra-prosthetic dislocation, which refers to the decoupling of the metal head (12) from the polyethylene insert (3). This occurs due to wear of the polyethylene rim (31), which gives stability to the head (12), due to friction and repetitive impact with the femoral neck (16). The results of this wear are evidenced in FIGS. 7A, 7B and 7C. The given reasons have limited the use of this type of implants to elderly patients or those at high risk of dislocation (Hamadouche et al. Is a Cementless Dual Mobility Socket in Primary THA a reasonable option. Clinical Orthopedics and related research 2012 (470): 3048. Philippot et al. Survival of Cementless dual mobility sockets with a mean 17 years follow-up Rev. Chir Orthop Reaparatrice Appar Mot 2008, 94 (8): e23).

Although joint wear with dual mobility cups has been difficult to assess, wear of the mobile ultra-high molecular weight polyethylene (UHMWPE) insert (3) in these implants is apparently similar to that of conventional UHMWPE cups. (Gaudin et al. Equivalent wear performance of dual mobility bearing compared with standard bearing in total hip arthroplasty: An in vitro study, Int Orthop. 2017 March; 41 (3): 521-527). Furthermore, Loving et al. demonstrated in hip simulators that highly cross-linked polyethylene in the dual mobility cups is more resistant to wear than fixed polyethylene of conventional cups in situations of overload due to increased inclination of the metal cup (edge loading). (Loving and Cols. Dual Mobility Bearings Withstand Loading from Steeper Cup-inclinations Without Substantial Wear. Journal of Orthopedic Research, 2015 (March): 398)

In summary, we can conclude that, despite the many alternatives that have been tried and the improvements that have been made to implants, there is a need in the current state of the art for hip protheses to have a protheses that allows the use of large heads in order to offer a greater range of movement and less risk of dislocation, without the problems derived from metal-metal combination and the use of very thin acetabular polyethylene.

During the decade of the 70s of the last century, the use of articulated polyethylene heads with metal cups in hip replacement was limited to resurfacing replacement and was abandoned because it presented a high rate of loosening and wear of high-density polyethylene (HDPE).

Other documents found in the state of the art refer to hip joint prostheses with polymeric heads that seek to overcome the deficiencies of the small diameter femoral head, in order to avoid severe abrasion and the ease of dislocation. Among them is the patent application US2014094927 that refers to a prosthesis for hip replacement that comprises a highly cross-linked polyethylene head from 28 mm to 48 mm in diameter and a cemented or uncemented metal cup, whose internal face is ultra-polished. By using a larger diameter head, the joint has a greater arc of movement and therefore greater stability. However, this application presents problems in the connection between the head and the stem, since it proposes a connector with a perimetral securing mechanism, structurally weak and lacking rotational and angular stability. Therefore, liable to generate debris and decoupling of the head.

To correct this problem, US2014094927 suggests improving the stability of the junction between the connector and the femoral component using biocompatible cement, adhesives or other "attachments", which are not secure coupling mechanisms for hip joint replacement. Furthermore, in the proposed connector design, it protrudes from the polymeric head, which may generate impingement on the acetabular rim. In addition to the above, if the connector proposed by US2014094927 penetrated deeper into the polymeric head, it would be, if necessary, very difficult to uncouple without damaging the polyethylene, due to the superior location of the proposed securing mechanism.

Likewise, patent application US 2017333192 proposes a prosthesis that combines a metal acetabular cup that has a smooth inner face and a large highly cross-linked polyethylene femoral head, which has an internal metal or ceramic core to assemble to the cone of the femoral component. However, this application does not propose any mechanism for securing the metal or ceramic core to the polyethylene head.

Another patent application related to polymeric heads is found in EP 2324800, which refers to a shoulder prosthesis, the characteristics of which could also be applicable to hip implants, as the inventors mention tangentially. This proposal comprises a metal cup and a large polymeric head with a rotationally stable metal substrate, which is assembled on the polymeric head during the manufacturing process with an injection mold, forming a solid head. The metal substrate is attached to a metal adapter that attaches the solid head to the humeral stem using Morse taper couplings.

This type of implant has several drawbacks for use as a hip replacement: (i) it is not advisable to use additional modularity in the femoral neck due to the risk of adverse tissue reactions to metallic debris (Cooper et al. Adverse Local Tissue Reaction Arising from Corrosion at the Femoral Neck-Body Junction in a Dual-Taper Stem with a Cobalt-Chromium Modular Neck. J Bone Joint Surg Am. 2013; 95: 865-72) and (ii) in case of removing the modular metal coupling and directly connecting the solid head to stem cone, a large inventory of heads would be required to adjust the length of the femoral neck.

In conclusion, in existing proposals, large head polymeric prostheses continue to present problems in securing the head to the connector. Due to these problems, the development of a modular polymeric prosthesis, with angular and rotational stable connector is required. Furthermore, this system should not introduce new metal-metal junctions that are inconvenient, and should offer the possibility of coupling the connectors for different neck lengths to heads of different diameters, and thus facilitate intraoperative adjustments according to the patient's requirements.

DETAILED DESCRIPTION OF THE INVENTION

Figure 1A:
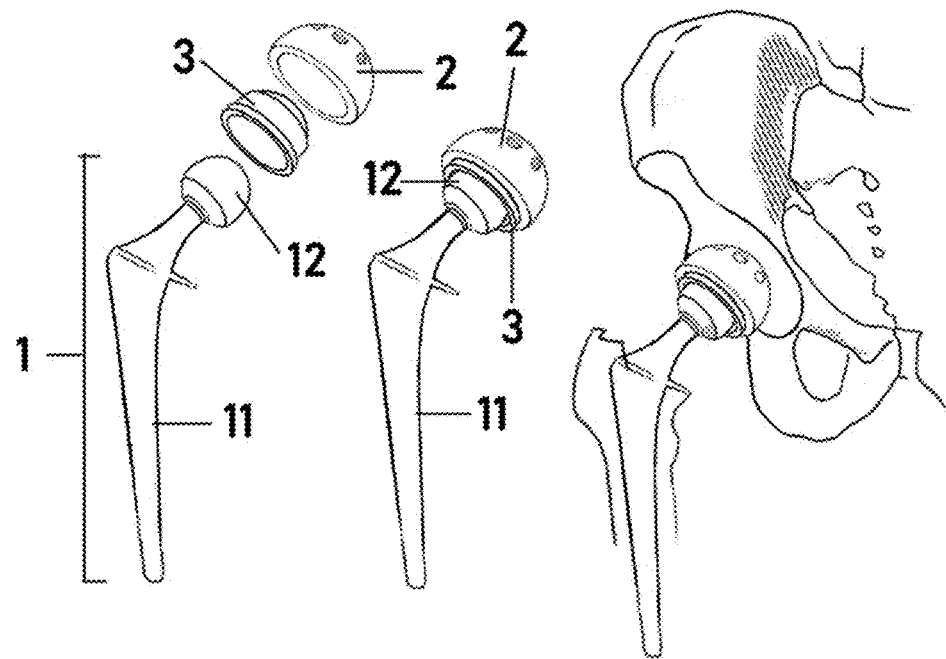
FIG. 1A. Prosthesis for total hip replacement with uncemented components.
Figure 1B:
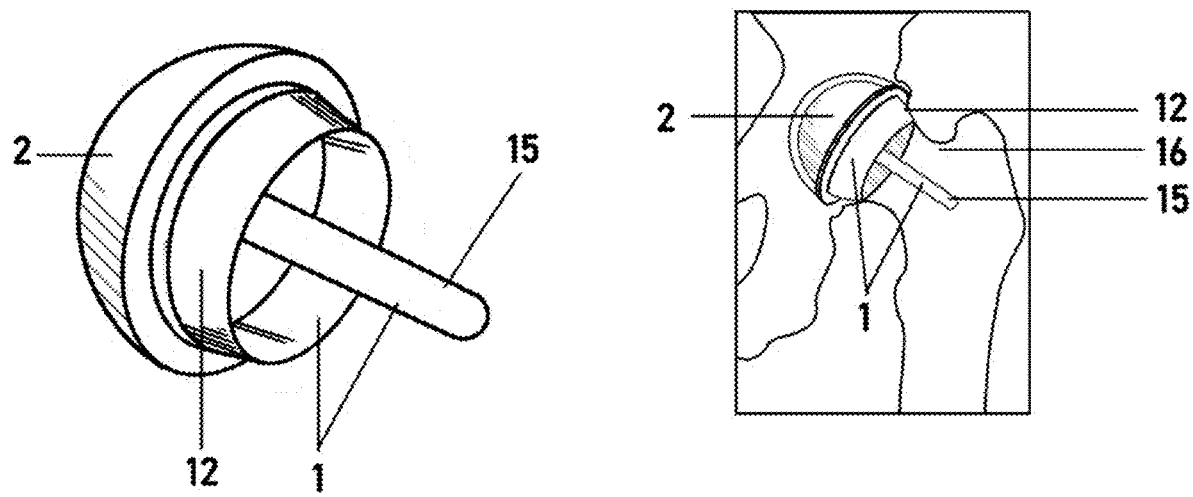
FIG. 1B. Prosthesis for hip resurfacing replacement.
Figure 2:
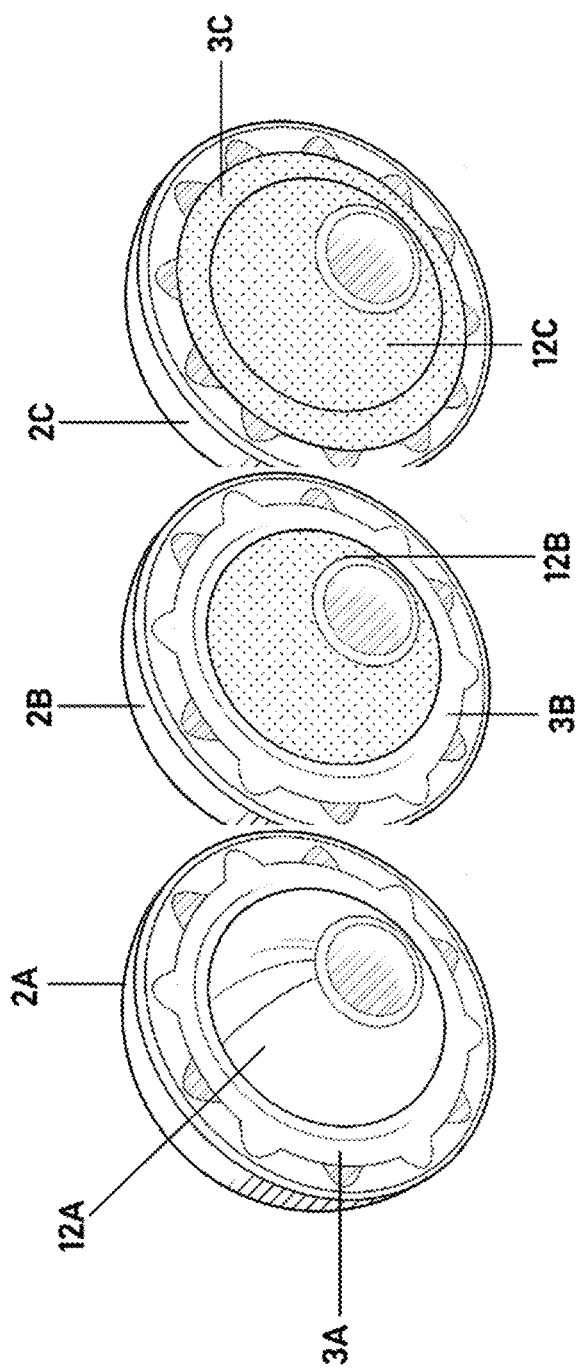
FIG. 2A. Cementless acetabular component with polyethylene insert and metal head.
FIG. 2B. Cementless acetabular component with polyethylene insert and ceramic head.
FIG. 2C. Cementless acetabular component with ceramic insert and ceramic head.
Figure 3:
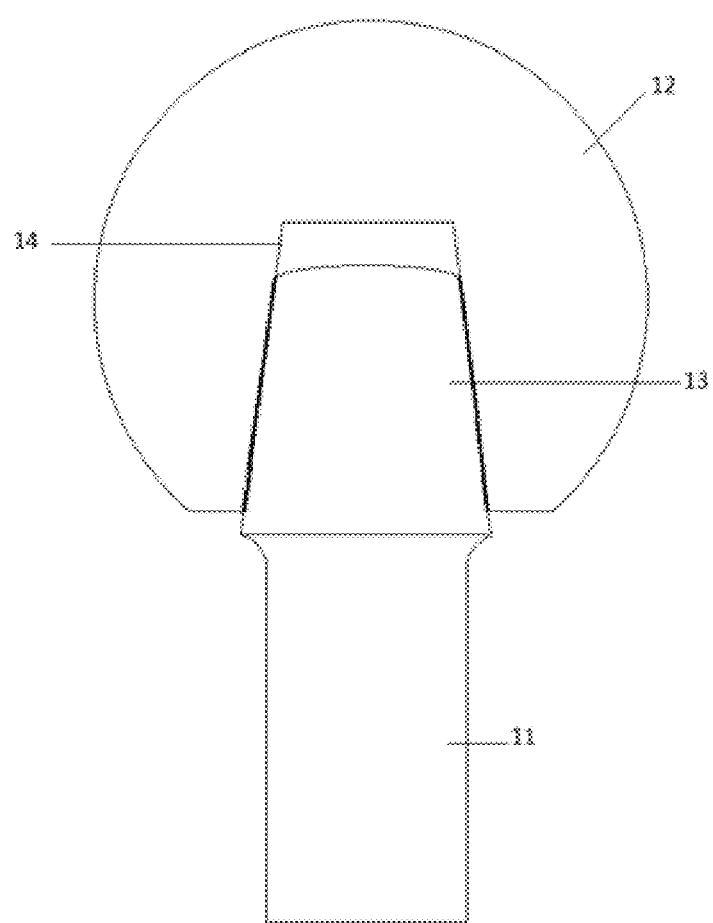
FIG. 3. Schematic of Morse taper in total hip replacement femoral head.
Figure 4:
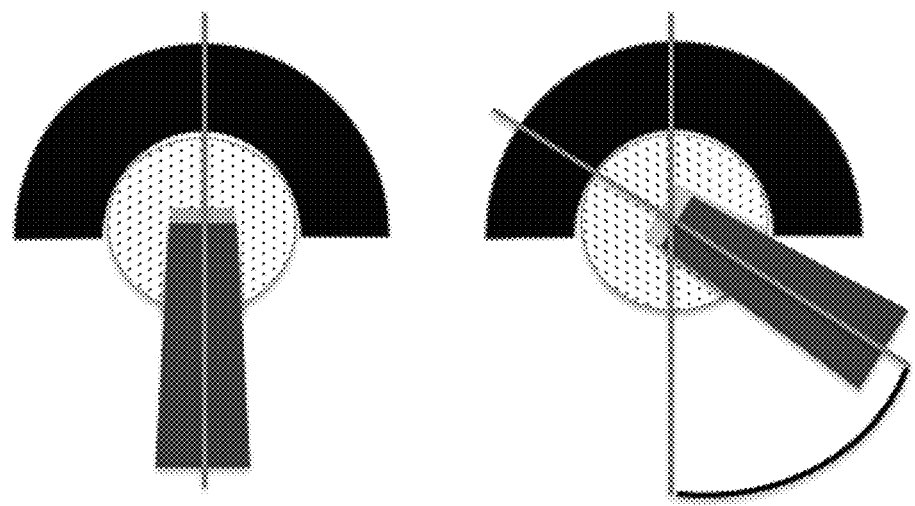
FIG. 4A. Arc of movement up to the impingement of the prosthetic femoral neck with the rim of the acetabular cup with a small head.
FIG. 4B. Arc of movement up to the impingement of the prosthetic femoral neck with the rim of the acetabular cup with a large head.
Figure 4:
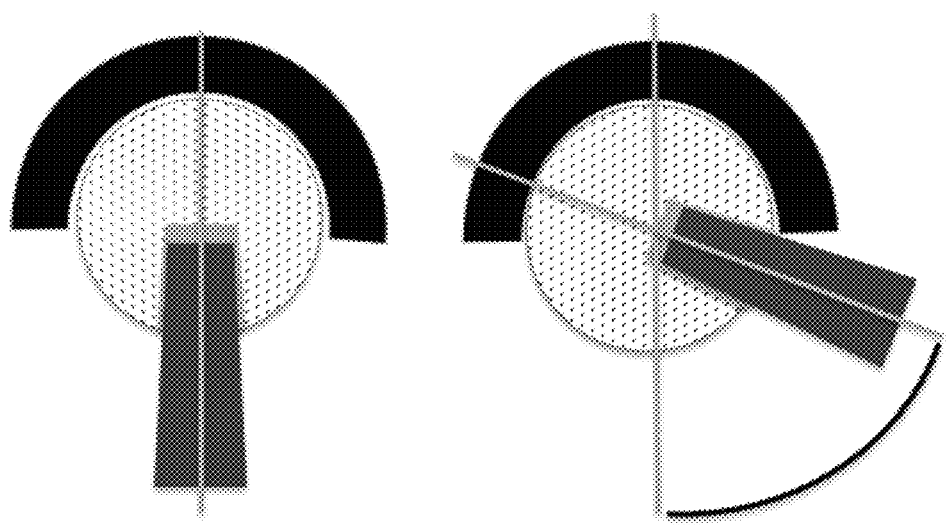
Figure 5:
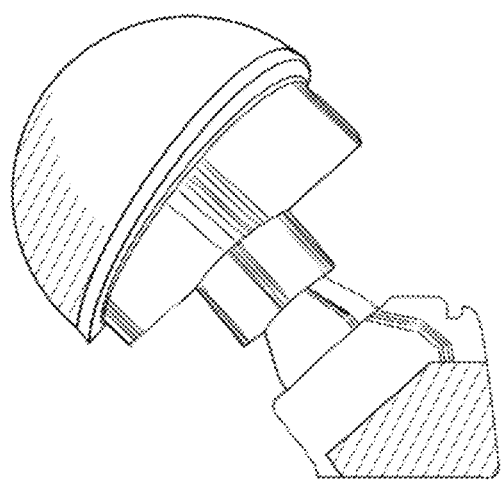
FIG. 5A. Metal-metal total hip prosthesis with large head.
FIG. 5B. Transmission scheme of the frictional torque to the Morse taper with large head.
FIG. 5C. Scheme of transmission of the frictional torque to the Morse taper with small head.
Figure 5:
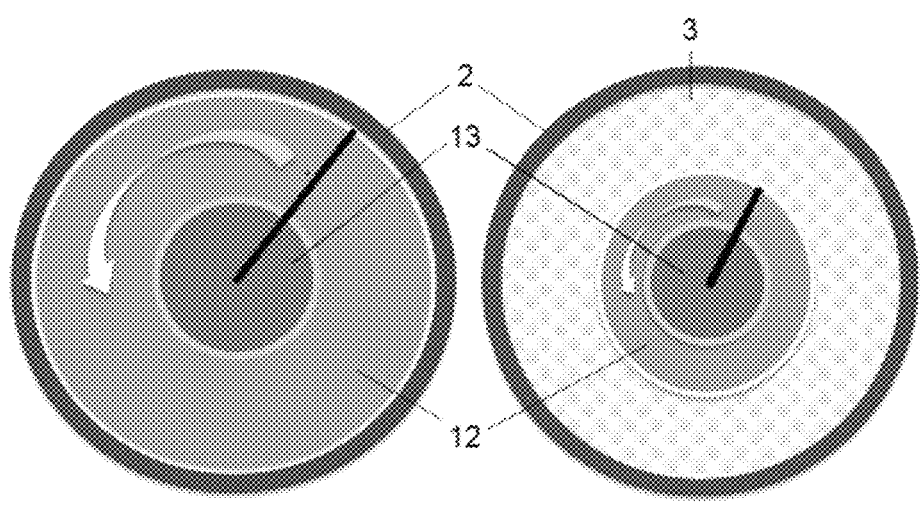
Figure 6:
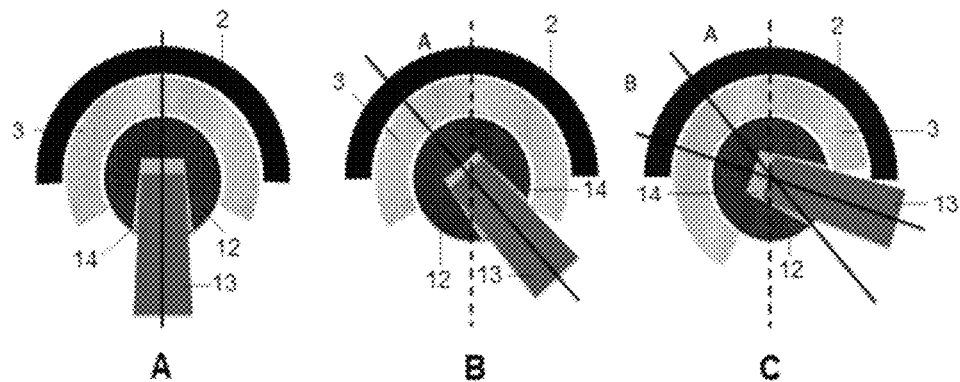
FIG. 6A. Scheme of the double mobility cup with the femoral component without flexion.
FIG. 6B. Scheme of the double mobility cup, showing the initial movement (A) between the metal head and the polyethylene core.
FIG. 6C. Scheme of the double mobility cup, showing the late movement (B) between the polyethylene core and the metal cup, after the contact of the neck of the femoral component hits the polyethylene rim.
Figure 7:
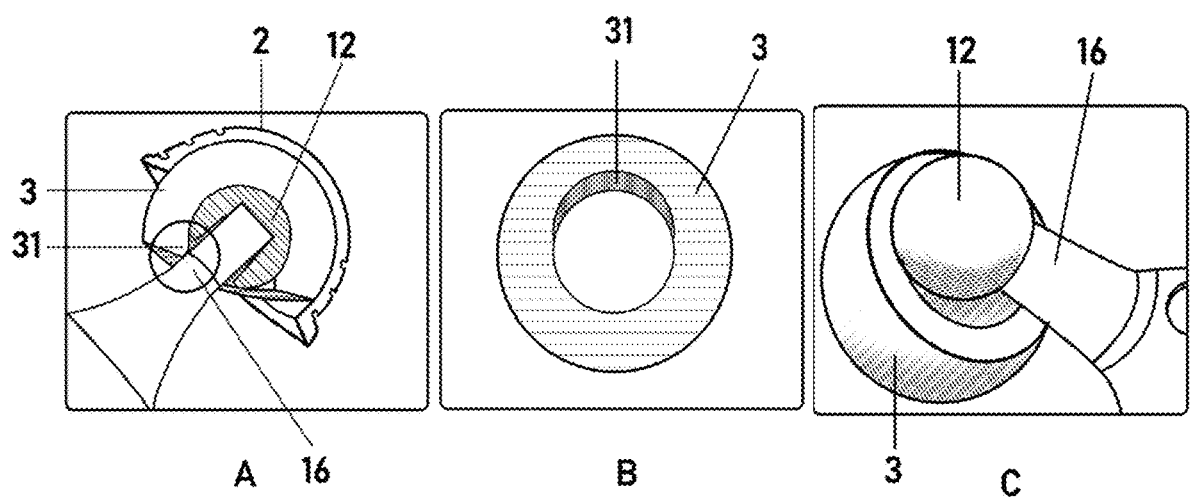
FIG. 7A. Contact of the femoral neck with the rim of the polyethylene core.
FIG. 7B. Wear of the capture rim of the mobile polyethylene mobile polyethylene core by repetitive shock and friction.
FIG. 7C. Intra-prosthetic dislocation: the metallic head comes out of the mobile nucleus of polyethylene due to wear of the rim.
Figure 8:
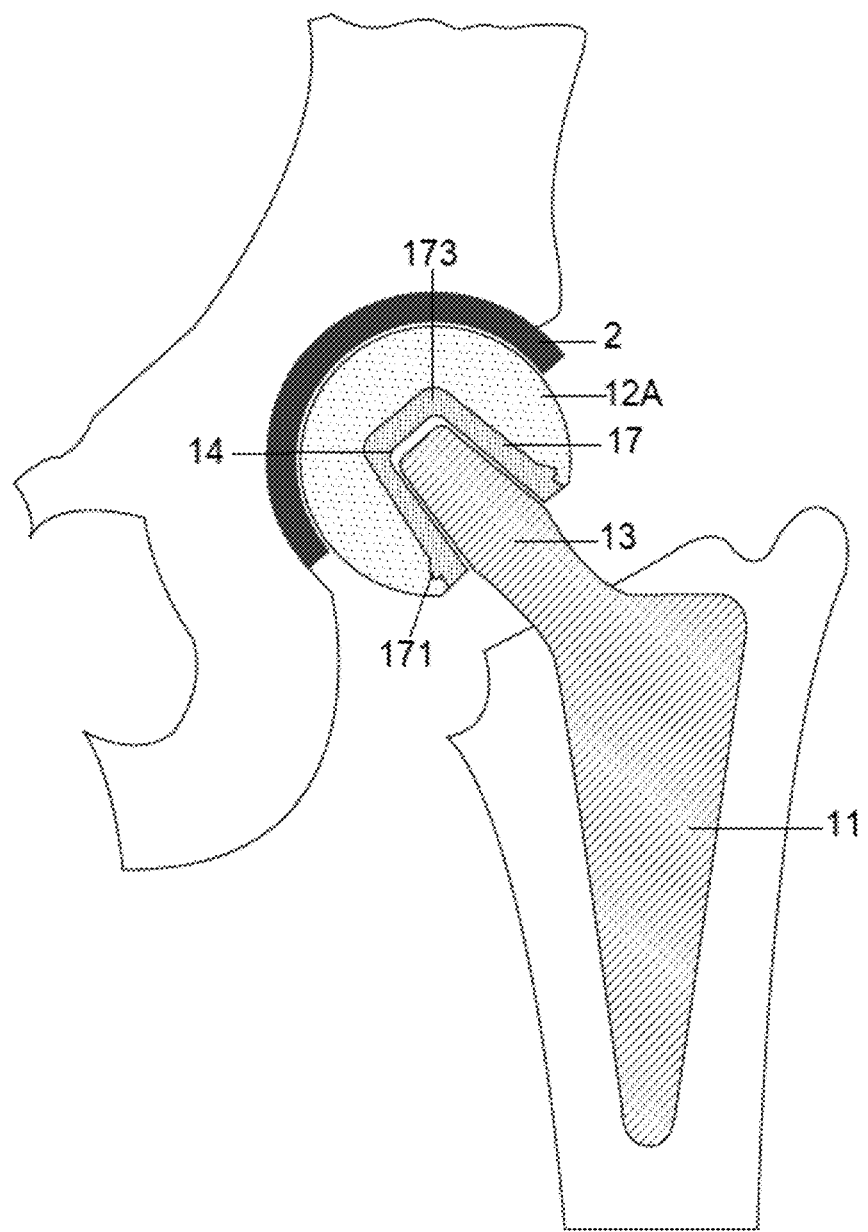
FIG. 8. Frontal longitudinal section of the hip with the prosthesis of the invention for total hip replacement.
Figure 9A:
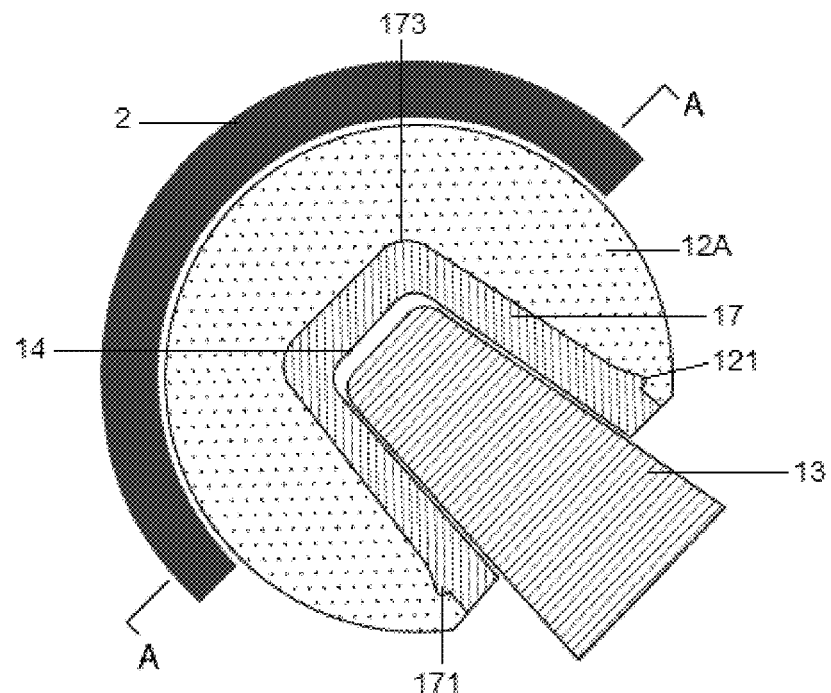
FIG. 9A. Longitudinal section of the prosthesis of the invention for total hip replacement, with a truncated pyramid-shaped anti-rotational connector core FIG. 9B. Cross section of the prosthesis of the invention, through A-A line of FIG. 9A, with an anti-rotational connecting core in the shape of a truncated pyramid with a hexagonal geometric shape.
Figure 17A:
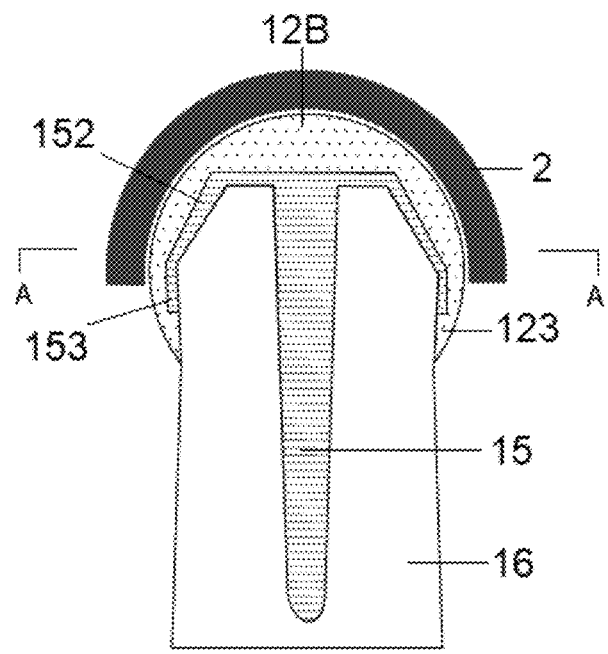
FIG. 17A. Longitudinal section of the femoral component of the prosthesis of the invention of FIG. 15 coupled to an acetabular component.
Figure 17B:
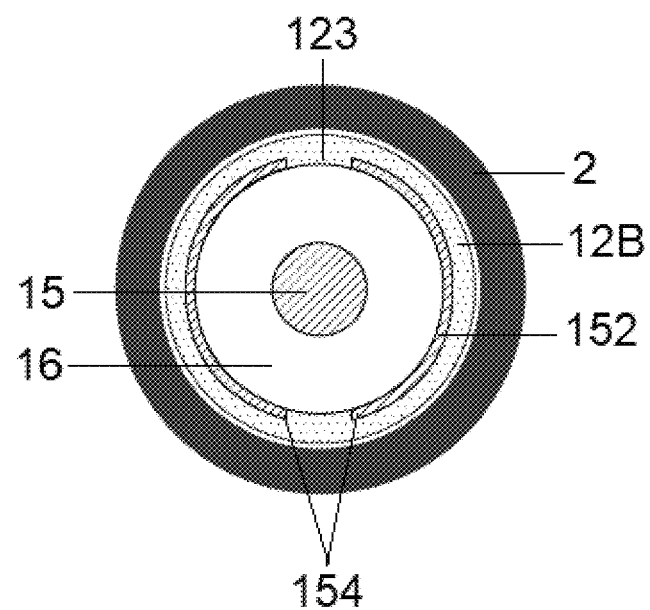
FIG. 17B. Cross section of the prosthesis of the invention, through line A-A of FIG. 17A.

The present invention relates to a hip replacement prosthesis comprising a highly cross-linked Polyethylene (HCLPE) polymeric femoral head, 38 mm to 64 mm in diameter (12A, 12B), which is characterized by containing a metallic or ceramic assembly (modular or not), with an axially and rotationally stable locking mechanism, to attach to the femoral component. This polymeric head is designed to articulate with a cemented or uncemented metal cup (2), whose internal face is ultra-polished, similar to the cups used in metal-metal implants or dual mobility implants, as shown in FIGS. 8, 9A, and 17A. That is, the invention consists of a polymeric head (12A, 12B) characterized by having an anti-rotational intra-prosthetic assembly to articulate with the femoral stem.

Highly Cross-Linked Polyethylene Head for Total Hip Replacement

In one embodiment of the invention, the polymeric head (12A) is part of a prosthesis to be used for total hip replacement, where the coupling mechanism to the femoral component is made using an anti-rotational connector core (17), stably assembled inside the polymeric head (12A), using a firm locking mechanism (171). This anti-rotational connector core (17) contains within it the female counterpart of the Morse cone (14) to couple with the male counterpart (13) of the upper end of the femoral component, as shown in FIGS. 8, 9A and 9B.

Figure 11:
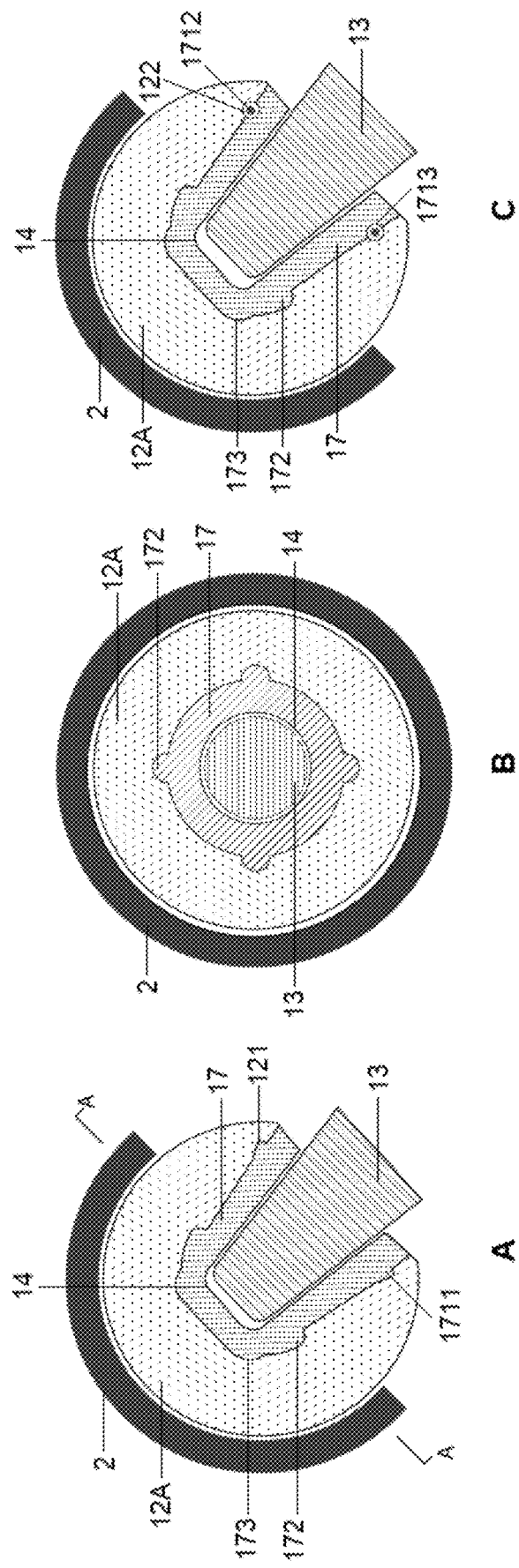
FIG. 11A. Longitudinal section of the prosthesis of the invention with the truncated cone shaped anti-rotational connector core with anti-rotatory fins, and a flange as an axial securing mechanism.
FIG. 11B. Cross section of the prosthesis of the invention, through line A-A of FIG. 11A, showing the anti-rotatory mechanism.
FIG. 11C. Longitudinal section of the prosthesis of the invention with the truncated cone shaped anti-rotational connecting core with anti-rotatory mechanism and with a metal ring as axial locking mechanism.
Figure 12:
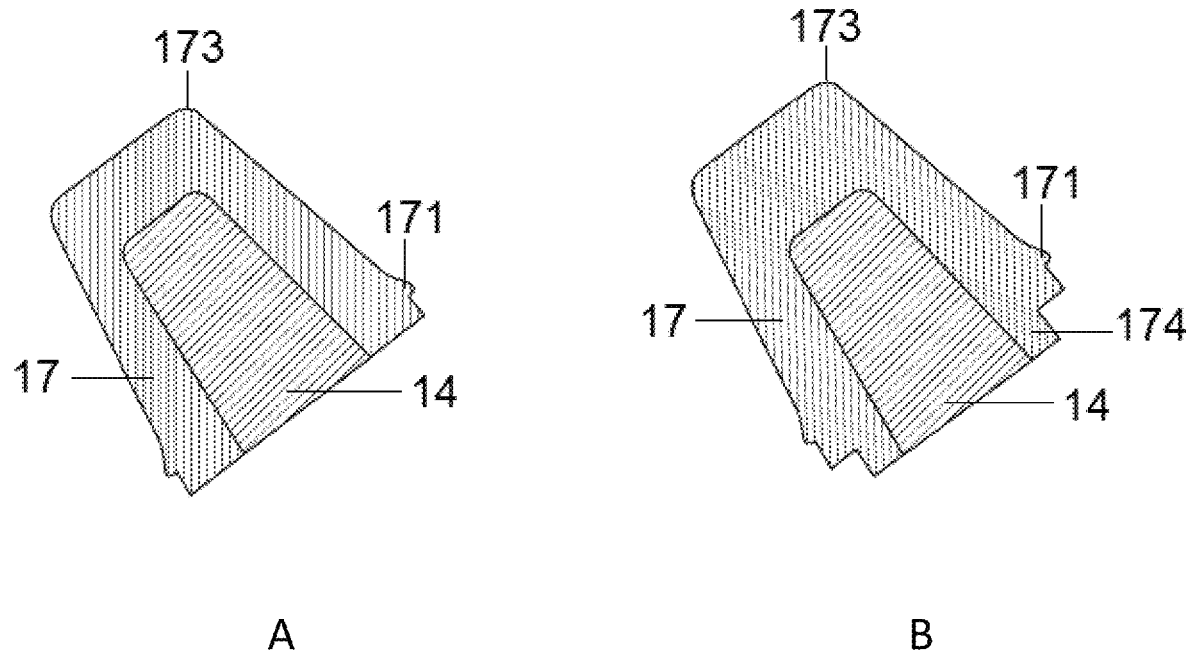
FIG. 12A. Longitudinal section of the anti-rotational connector core without extension, to be assembled on the polyethylene head.
FIG. 12B. Longitudinal section of the anti-rotational connector core with skirted extension to be assembled to the polyethylene head.

Said anti-rotational connecting core (17) is characterized in that it has the shape of a truncated polyhedral pyramid, selected from the group consisting of a square, pentagonal, hexagonal, heptagonal, octagonal, etc. shape, as illustrated in the FIGS. 9A, 9B, 10A, 10B, 10C and 10D. The external shape of the anti-rotational connecting core (17) can also correspond to a truncated cone shape as shown in FIGS. 11A, 11B and 11C. Regardless of the shape of said pyramid or cone, the longitudinal section of the anti-rotational connector core (17) corresponds to a trapezoidal shape.

Figure 9B:
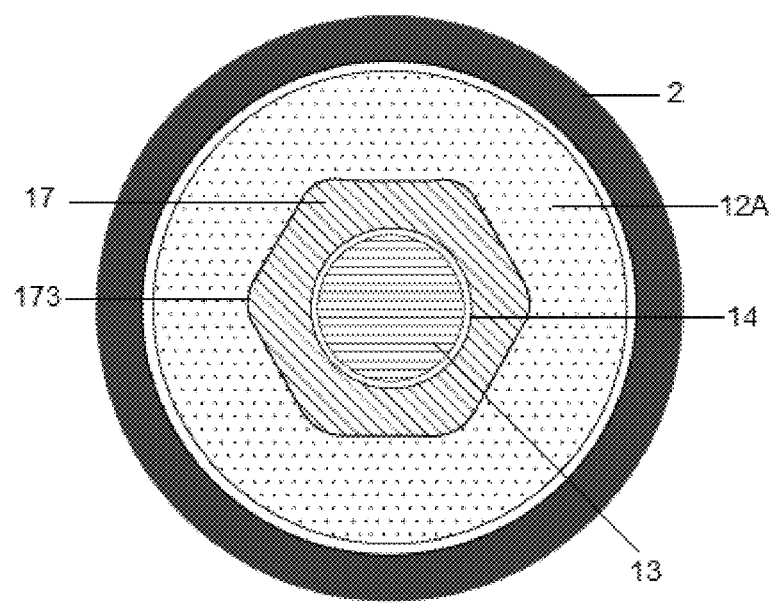
Figure 10:
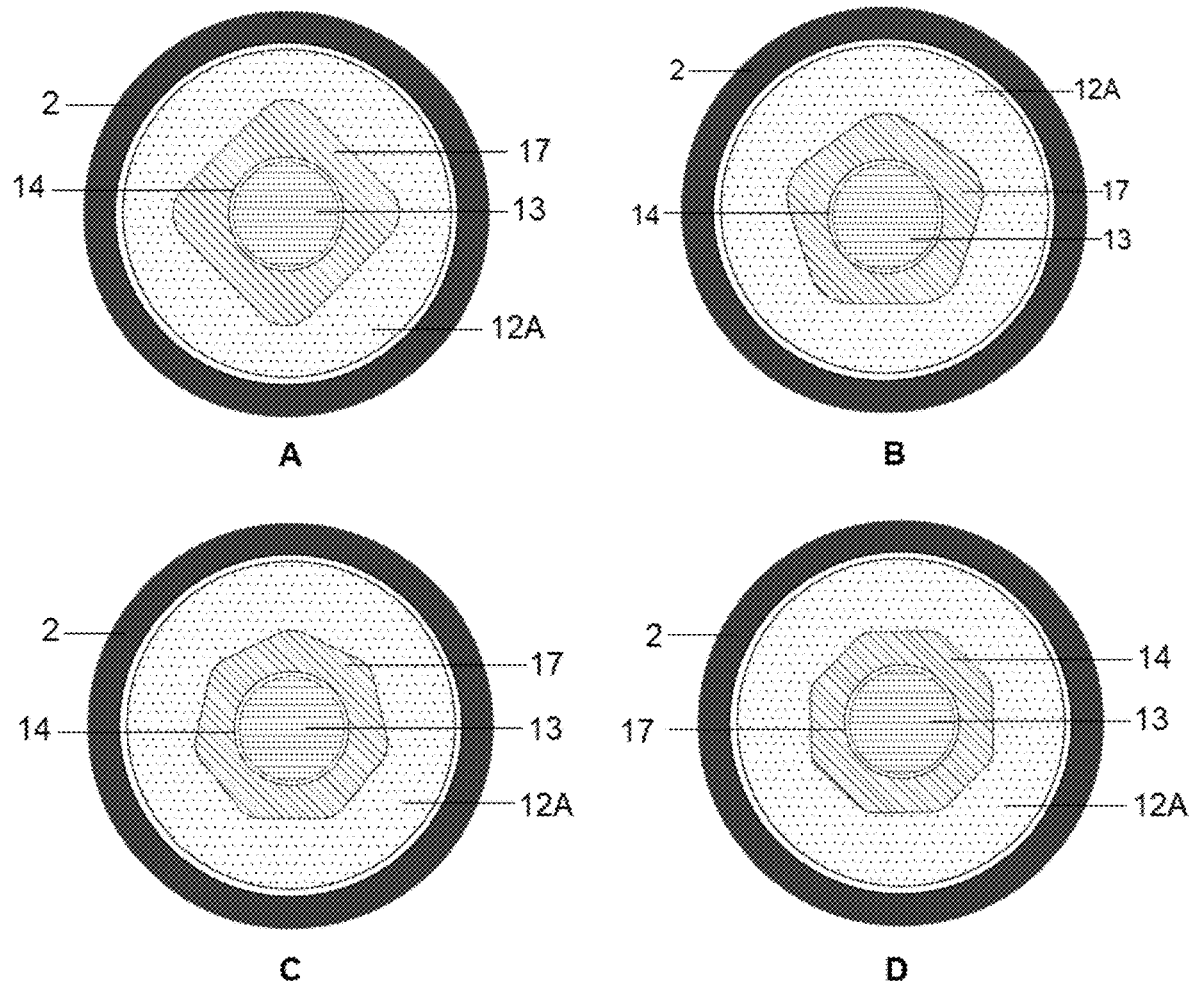
FIG. 10A. Cross section of the prosthesis of the invention, where the head has a truncated pyramid-shaped anti-rotational connector core with a square geometric shape.
FIG. 10B. Cross section of the prosthesis of the invention, where the head has an anti-rotational connecting core in the form of a truncated pyramid with a geometric pentagonal shape.
FIG. 10C. Cross section of the prosthesis of the invention, where the head has an anti-rotational connecting nucleus in the shape of a truncated pyramid with a heptagonal geometric shape.
FIG. 10D. Cross section of the prosthesis of the invention, where the head has an anti-rotational connecting core in the shape of a truncated pyramid with an octagonal geometric shape.

In a preferred embodiment of the invention, the anti-rotational connecting core (17) has the shape of a truncated hexagonal pyramid, where the longitudinal section of the anti-rotational connecting core (17) corresponds to a truncated cone and the core has a hexagonal shape in the transverse plane, as evidenced in FIG. 9B. Said core (17) is coupled to the polymeric femoral head (12A), within an internal cavity in said head, that has the same geometric shape, and is press-fitted.

In a preferred embodiment, said anti-rotational connecting core (17) is fixed inside the head (12A) by means of a locking mechanism, which consists of a flange (171) that projects perimetrically on the external surface of the anti-rotational connecting core (17) and fits in a slot (121), located in the internal space of the polymeric head (12A), as illustrated in FIGS. 8 and 9A. In this way, the axial stability of the anti-rotational connector core (17) is achieved and the rotational stability is provided by the geometric shape of the core, avoiding movement and the production of wear particles. The shape and size of the core allow complete contact of its walls and roof with the interior of the polymeric head, avoiding the presence of spaces that allow deformation of the polymer by loads. This core can be made of metal or ceramic alloys and can be assembled to the polymeric head either at the factory or produced separately and coupled during surgery. This last alternative has the advantage of reducing the inventory of polymeric heads necessary for each surgical procedure, since connector cores of different femoral neck lengths could be used for each head diameter and the same cores can be used for heads of different sizes.

In another alternative of the invention, the anti-rotational connecting core (17) has a truncated cone shape and the longitudinal section corresponds to a trapezoidal shape, but the core has a round shape in the transverse plane, as illustrated in FIGS. 11A and 11B. In this case, the implant includes an anti-rotatory mechanism (172), consisting of 1 to 6 longitudinal fins on the external surface of the anti-rotational connector core (17), and an axial securing mechanism that is selected from a beveled perimeter flange (1711) which fits into the perimeter groove (121) in the interior space of the head (12A), shown in FIG. 11A; or a metal ring (1712) that is located between a perimeter groove (1713) in the core (17) and a perimeter groove (122) in the interior space of the head (12A) represented in FIG. 11C.

In addition to the aforementioned characteristics, the anti-rotational connector core (17) of the prosthesis, in any of its modalities, has always rounded corners (173), to avoid stress concentration zones, as seen in FIGS. 8 to 12.

Likewise, the anti-rotational connector core may have an extension or skirt (174) of the Morse taper, as illustrated in FIG. 12B. Said extension or skirt (174) is intended to improve the versatility of the prosthesis by allowing the length of the prosthetic femoral neck to be increased a bit more, similar to what in conventional metallic femoral heads is called skirted heads.

Now, in order to provide adequate stiffness to the implant, the walls of the anti-rotational connector core (17) must have a thickness between 4 mm and 8 mm, to avoid deformations in their coupling to the femoral cone. This core is made of a material selected from the group consisting of chrome-cobalt alloys, titanium alloys or stainless steel, but it can also be made of ceramic.

The polymeric head is preferably made of Highly Cross-linked Polyethylene (HCLPE).

Figure 13A:
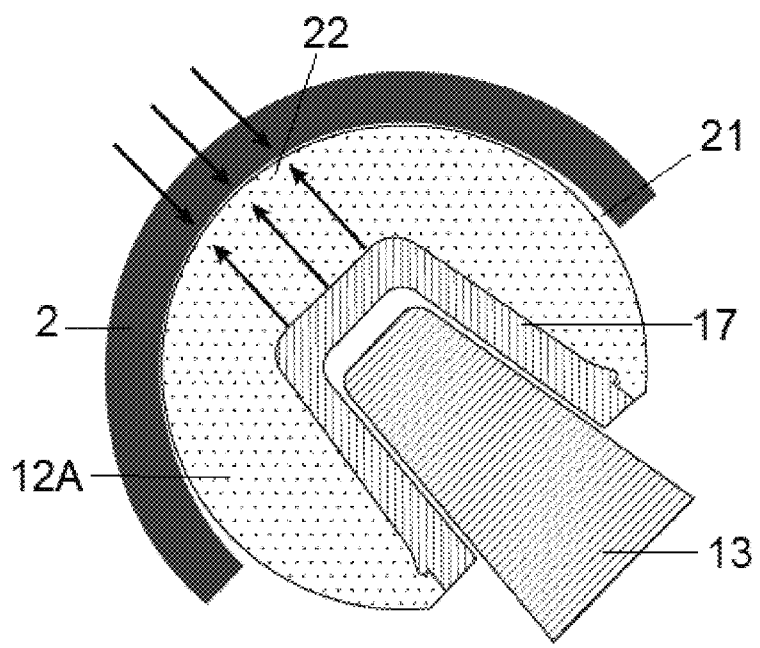
FIG. 13A. Clearance between the cup and the head where its greatest contact is polar.
Figure 13B:
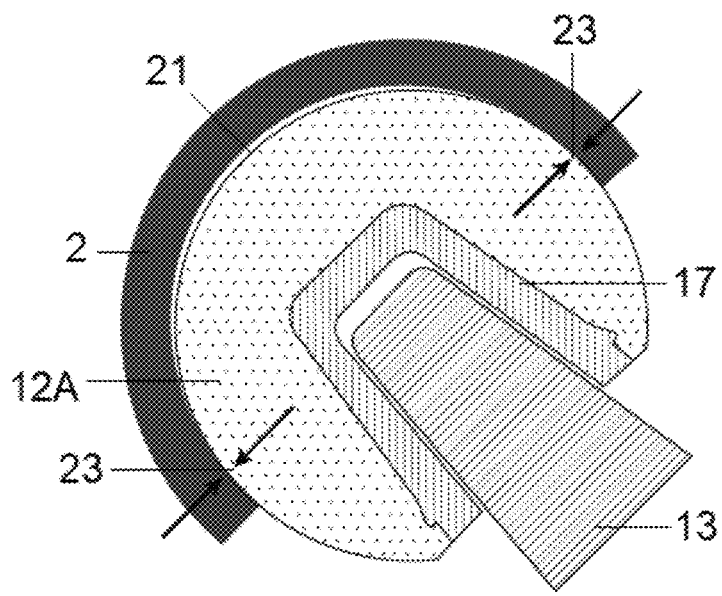
FIG. 13B. Clearance between the cup and the head where its greatest contact is equatorial.

As for the radius of curvature (21) of the polymeric head (12A, 12B), it must have a tolerance in relation to the internal diameter of the cup, between 50 and 150 microns, which allows more polar contact (22) than equatorial (23) in the acetabular cup, as illustrated in FIG. 13A. The latter, in order to avoid friction zones in the equatorial area and achieve a better load transmission and lubrication.

Due to the properties of the invention, the total hip replacement prosthesis of the present invention has utility in the following situations:

1. Total primary hip replacement procedures, especially in older patients or those at high risk of dislocation.

2. The polymeric head can be articulated, either with a solid metal uncemented cup; with an uncemented metal cup with holes for screw fixation and modular metal insert; or with cemented metal cups. All of these cup options include ultra-polished metal articular surface, similar to cups used with metal-to-metal or dual mobility implants.

3. Likewise, the prosthesis is ideal for total hip replacement revision surgeries, using either a metal cup without holes; or modular cups with metal inserts or cemented metal cups with or without a reinforcing ring.

4. Likewise, the prosthesis can be used in large head metal-metal total hip replacement revision surgeries or in double mobility cup revision surgeries, preserving the original acetabular prosthetic component.

5. It can also be used in revision hip replacement surgeries while retaining the original acetabular prosthetic component.

Highly Cross-Linked Polyethylene Head for Hip Resurfacing Replacement

Figure 14A:
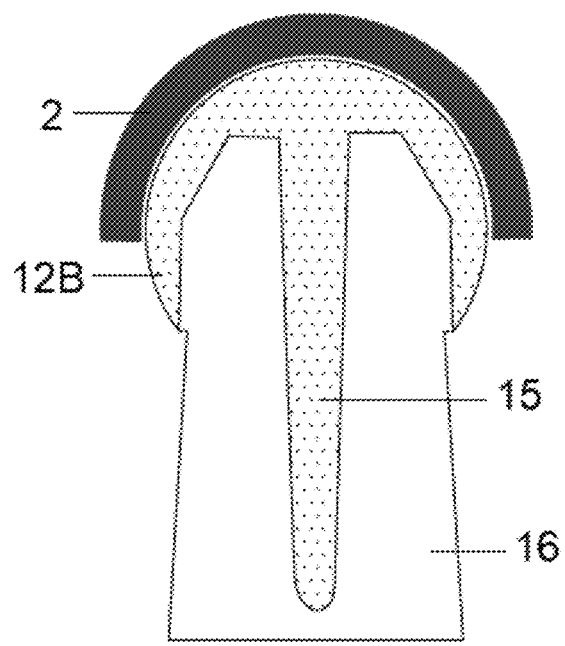
FIG. 14A. Longitudinal section of the prosthesis of the invention for hip resurfacing replacement made of polyethylene.

In the other embodiment of the present invention, the prosthesis intended for hip resurfacing replacement is characterized in that the polymeric prosthetic femoral head (12B), with a diameter between 40 mm and 64 mm, has a lower extension or stem (15), which allows fixation to the femoral neck (16) with or without bone cement. Said femoral head (12B) articulates with an ultra-polished metallic acetabular component (2), as shown in FIG. 14A. In this embodiment of the invention, the fixation of the head (12B) to the femur is carried out with cement and the fixation of the acetabular component (2) can be cemented or uncemented.

Figure 14B:
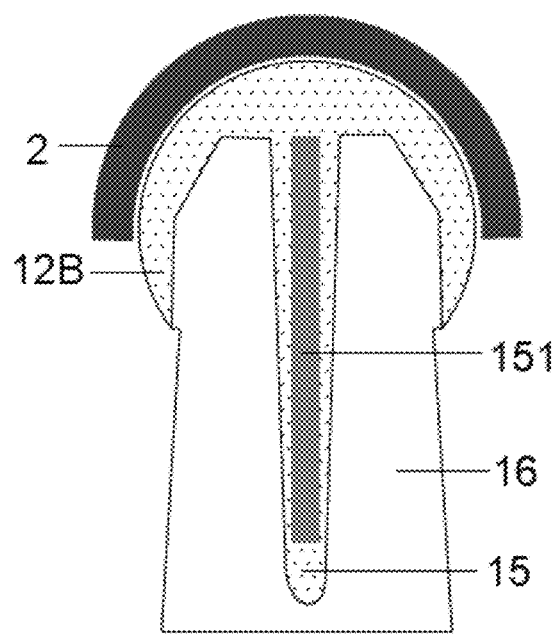
FIG. 14B. Longitudinal section of the prosthesis of the invention for hip resurfacing replacement made of polyethylene with internal metallic reinforcement in the femoral neck.
Figure 15:
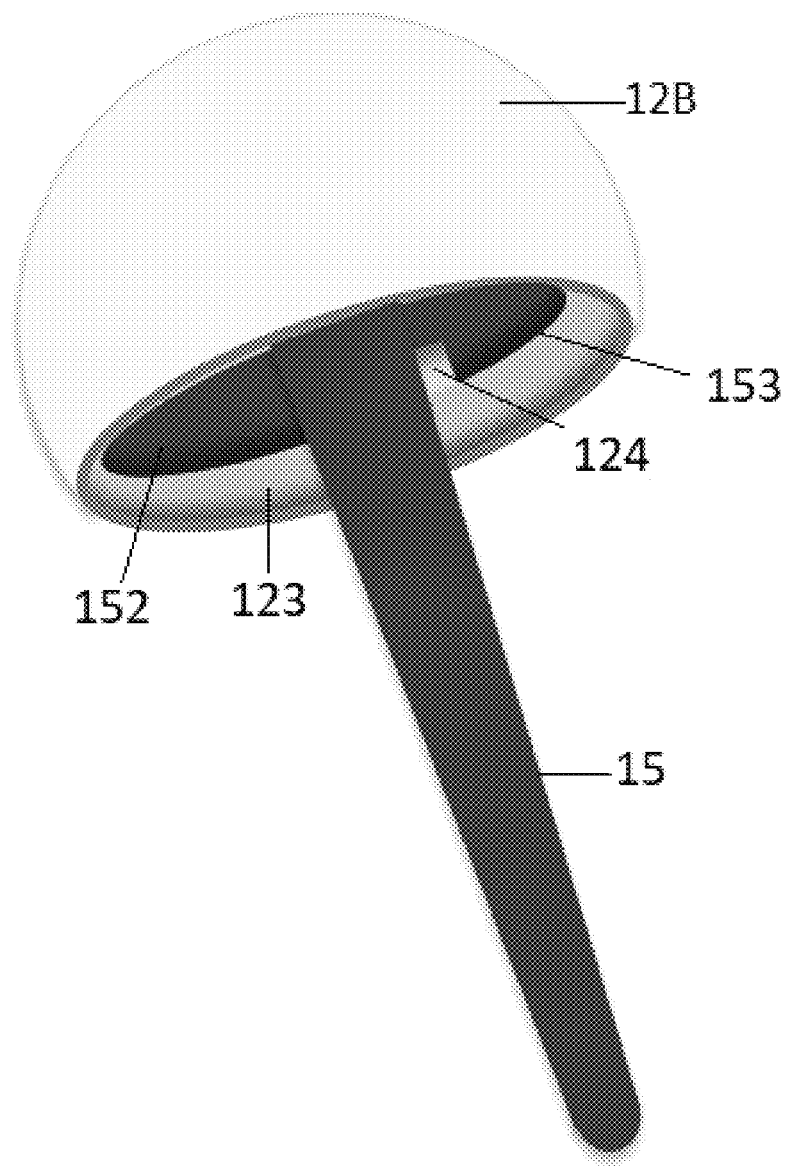
FIG. 15. Perspective of the femoral component of the prosthesis for hip resurfacing replacement made of polyethylene with anti-rotational metal-back.
Figure 16:
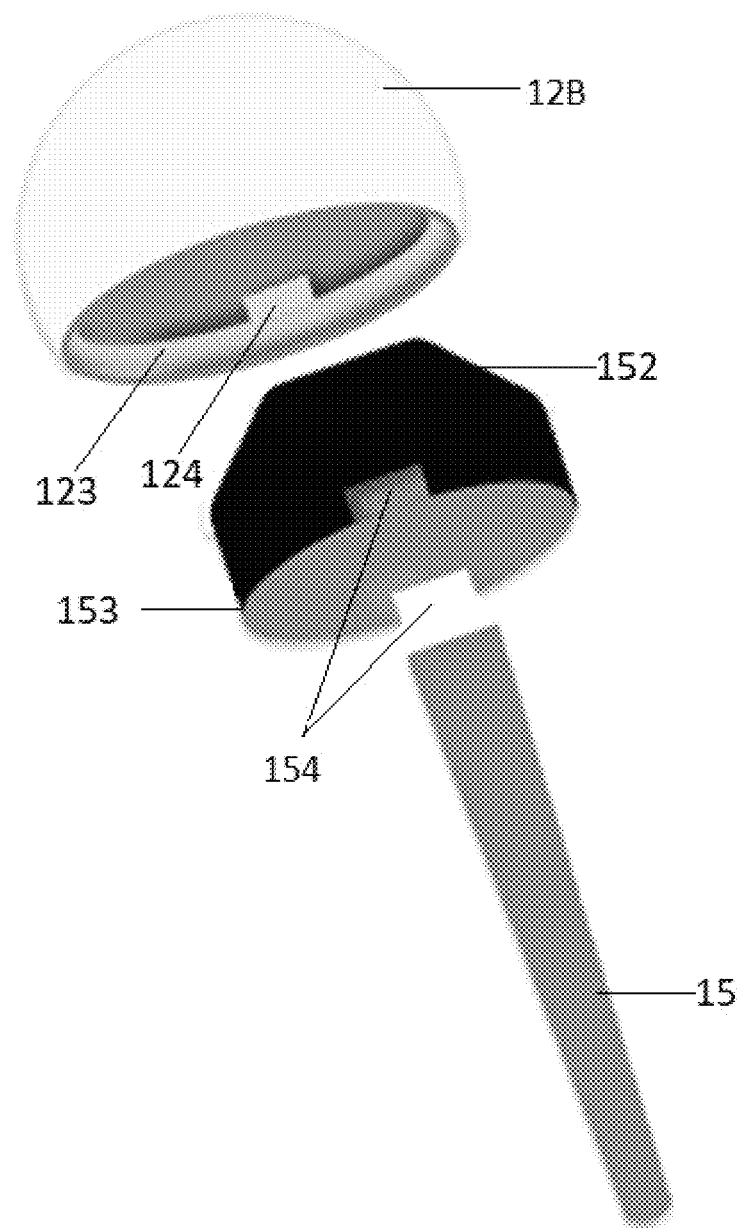
FIG. 16. Breakup view of the femoral component of FIG. 15. For the purposes of the representation, the stem has been separated from the metal-back.

In another alternative of this embodiment, the extension or lower stem (15) of the prosthetic femoral head (12B) can be made entirely of polyethylene or it can be made of polyethylene with an internal metal reinforcement (151), as illustrated in the FIGS. 14A and 14B, respectively.

In the preferred alternative of the prosthesis intended for hip resurfacing replacement, the implant of the invention comprises the polymeric head (12B) with a thin metal-back (152) attached to a metal stem (15), as shown in the FIGS. 15, 16, 17A and 17B. In order not to thin down the polyethylene, the metal-back (152) must have a thickness between 2 and 3 mm, preferably 2 mm.

In this embodiment of the invention, the polymeric head (12B) is secured to the metal-back (152) by means of an anti-rotational intra-prosthetic assembly, characterized by a circumferential flange (123) located inside the head which fits securely in the lower edge (153) of the metal-back (152), thus preventing the axial movement of the head (12B). Rotational stability is given by 2 to 4 anti-rotatory tabs (124), preferably 2 tabs, which project from the inner face of the polymeric head (12B) as an extension of the upper edge of the circumferential flange (123), one opposite to the other which fits into corresponding notches (154) located on the lower edge (153) of the metal-back (152).

The metallic stem and the metal-back can be made with external porous coating for uncemented use, or without porous cover for cemented fixation.

For better rotational stability, the stem (15) used in the cemented fixation of the femoral component, in any of its modalities, is conical or tapered in a rectangular geometric shape with rounded corners and tips (not sharp), to avoid stress areas in the cement mantle.

Likewise, the internal face of the polymeric head (12B) or the metal-back that will be in contact with the bone cement must have irregularities (grooves or grids not shown in the figures) for better interdigitation of the cement and rotational stability.

Due to the properties of the invention, the hip resurfacing replacement implant is useful in the following situations:

1. Primary hip replacement in young patients.

2. Primary hip replacement in cases of proximal femur deformity due to osteotomy or old fracture.

3. Primary hip replacement in patients with a high risk of dislocation.

In order to clearly delimit the scope of the present invention, some terms which have been used in the description of the invention and which facilitate its understanding are specified below.

Press-fit. It refers to the stability or initial grip mechanism of the prosthesis, which provides the necessary stability to allow osteo-integration of the prosthesis. It is generally performed by preparing a bed slightly smaller in size than the final implant, so that the latter fits snugly, preventing axial, angular and rotational movements.

Hip joint. It is the site of union between the pelvis and the femur. The spherical head of the femur fits into the acetabular cavity of the pelvis and is the site of movement between the lower extremity and the pelvis. The term joint is also used to refer to the site of movement between the prosthetic head and acetabulum of total hip replacement.

Total hip replacement revision surgery. A surgical procedure that is performed to change partially or completely the components of a total hip replacement.

Femoral component. Refers to the prosthetic implant that is placed in the medullary canal of the superior end of the native femur in the hip replacement. Generally, the prosthetic head is modular and adapts to the prosthetic stem using a Morse taper mechanism.

Cemented femoral component (cemented femoral stem). Refers to femoral prostheses made to be implanted using bone cement (polymethylmethacrylate). These implants have a smooth or less rough surface and their fixation is always done with bone cement.

Uncemented femoral component (uncemented femoral stem). This refers to the porous-coated femoral prosthesis for osteointegration, which is implanted in the femur in total hip replacement.

Morse taper. It is the mechanism used to attach the prosthetic modular femoral head to the upper end or neck of the femoral stem. This ends in a segment in the form of a truncated cone (male), whose length is variable. The cone fits into the femoral head, which has a socket (female) with the same geometric shape and angulation. Its adjustment is made by impacting the head on the male component of the neck.

Acetabular cup. It is the component of a hip replacement prosthesis that is placed in the acetabular cavity of the pelvis. There are uncemented cups which are composed of a metallic cup with an external porous coating, generally hemispherical, and a modular component of polyethylene, ceramic or metal, which is assembled in the concavity of said cup. There are also cemented acetabular cups which are made entirely of polyethylene and are fixed to the bone with bone cement.

Linear wear. It refers to the magnitude of penetration of the prosthetic femoral head into the prosthetic articular acetabular surface as a consequence of material wear. It is generally expressed in millimeters.

Volumetric wear. It is the term used to quantify the volume of material removed from polyethylene or any other articular surface generated by movement and loads on the joint. The volume of polyethylene removed for an equal amount of penetration of the femoral head is greater in heads with a larger diameter.

Debris. Those are the wear particles that are released on the movement surfaces of the prostheses. There are polyethylene, metal or ceramic debris.

Intra-prosthetic dislocation. It is a term used to describe the unique situation of dual mobility hip replacements in which the femoral head is decoupled from the mobile polyethylene insert. This occurs because the polyethylene containment mechanism is lost due to wear.

Prosthetic dislocation. It is the situation in which the femoral head of the total hip replacement is decoupled from the acetabular component when taken to extreme movements, since there is normally no mechanism for containing the head within the acetabular cavity.

Modular. Refers to prosthetic components made up of separate parts that are assembled during surgical implantation. For example, the acetabular component has an internal insert of polyethylene or ceramic that is assembled in the metal cup after placing it in the native acetabulum. This has two purposes, one is to allow the placement of the screws to fix the cup to the bone through holes in it and the other is to be able to use polyethylene with projections, eccentricity, lateralized as needed; or inserts made of ceramic or metal. Likewise, the prosthetic femoral head is modular with the body of the prosthesis, and its coupling is carried out by means of a Morse taper mechanism (male component-female component). This allows the length of the femoral neck to be modified according to the depth of the taper in the prosthetic head.

Osteo-integration. It refers to the process of bone growth on the porous covering of uncemented implants. When the bone growth on the cover is sufficient to provide stability to the implant, it is considered to be osteo-integrated.

Highly Cross-linked Polyethylene (HCLPE). Refers to a polymeric material made of high molecular weight polyethylene, which has been subjected to a process of irradiation with gamma rays or electron beams and heating, in order to produce crosslinking of the polymer chains. Both in hip simulators and in vivo wear measurements, a significant reduction in the amount of wear has been shown when used in the acetabular components of the total hip replacement.

Local corrosive processes. It refers to the processes of galvanic and crevice corrosion that occur in the metal-metal modularity sites, which end up releasing corrosion products, ions and metal particles to peri-prosthetic fluids and tissues, generating a local biological reaction and also, systemic repercussions (generalized or in distant organs).

Adverse tissue reactions. Refers to the biological reaction process of tissues around prosthetic components in response to metal ions or to the deposition of polyethylene or metal particles resulting from wear. This reaction can lead to bone resorption or the formation of pseudo tumors.

Porous coating. It refers to the coating that the uncemented implants have on the external surface that is in contact with the native bone. There are several types of porous coatings and their function is to allow bone growth within the pores or surface irregularities, to give implants long-term stability.

Peri-prosthetic tissues. It is used to refer to the bone and soft tissues adjacent to the implant, both in the femur and in the pelvis. The wear debris of the materials of the joint replacements are mainly deposited in these tissues.

Clearance. It refers to the difference in the radius of curvature of the acetabular cavity and the femoral head of the prosthesis. Low tolerance joints increase friction on the surface and make lubrication difficult.

The invention claimed is:

1. Hip replacement prosthesis characterized in that it comprises a highly cross-linked polyethylene (HCLPE) head from 38 mm to 64 mm in diameter with an anti-rotational intra-prosthetic assembly provided by an anti-rotational connecting core which is fitted entirely inside the head, inside a cavity with the same geometric shape of the connecting core, and is fixed to said cavity by means of an axial locking mechanism that is located in a lower third of the external surface of the connecting core, such anti-rotational connecting core being shaped as a truncated polyhedral pyramid or is a truncated cone with longitudinal fins located on a central or upper third of an exterior surface of the truncated cone.

2. The prosthesis according to claim 1, characterized in that it is a total hip replacement prosthesis comprising a femoral component consisting of a femoral stem that contains in its upper end a male counterpart of a Morse-taper junction in which the polyethylene head is assembled by means of the anti-rotational connecting core, which contains a Morse taper female counterpart to mate with the male counterpart of the femoral component.

3. The prosthesis according to claim 2, characterized in that the anti-rotational connector core has an extension or skirt, which lengthens it and distally translates the position of the female component of the Morse taper.

4. The prosthesis according to claim 1, characterized in that the rotational stability is given by the polyhedral pyramid shape of the anti-rotational connecting core which is selected fern the group consisting of a square, pentagonal, hexagonal, heptagonal shape or octagonal.

5. The prosthesis according to claim 4, characterized in that the polyhedral pyramid shape of the anti-rotational connecting core is hexagonal.

6. The prosthesis according to claim 1, characterized in that the axial locking mechanism of the anti-rotational connecting core is a perimeter beveled flange, which projects into the lower third of the outer surface of the anti-rotational connecting core and it is inserted in an also perimeter groove, located in the internal space of the head.

7. The prosthesis according to claim 1, characterized in that the axial locking, mechanism of the anti-rotational connector core is a perimeter wire that fits into also perimeter grooves, located at the same level, one, in the internal space of the head and the other, in the external surface of the anti-rotational connector core.

8. The prosthesis according to claim 1, characterized in that the anti-rotational connecting core is a truncated cone and comprises 1 to 6 longitudinal fins located in the central third or in the upper third of its external surface for rotational stability.

9. The prosthesis according to claim 1, characterized in that the walls of the anti-rotational connecting core have a thickness between 4 mm and 8 mm.

10. The prosthesis according to claim 1, characterized in that the corners of the anti-rotational connecting core are rounded.

11. The prosthesis according to claim 1, characterized in that the anti-rotational connecting core is made of a material selected from the group consisting of chromium-cobalt alloys, titanium alloys, stainless steel or ceramic.

12. The prosthesis according to claim 1, characterized in that it further comprises a cemented or uncemented metal cup, which internal surface which is ultra-polished.

13. The prosthesis according to claim 12, characterized in that a radius of curvature of the polyethylene head is less than a radius of curvature of the interior of the metal cup, and contact of the head with the metal cup is more polar than equatorial.

* * * * *